(12) United States Patent
Burke et al.

(10) Patent No.: US 8,696,627 B2
(45) Date of Patent: Apr. 15, 2014

(54) TWO WAY ACCUMULATOR PROGRAMMABLE VALVE PUMP

(76) Inventors: Paul Burke, Bellingham, MA (US); Patrick O'Connor, North Attleboro, MA (US)

( * ) Notice: Subject to any disclaimer, the term of this patent is extended or adjusted under 35 U.S.C. 154(b) by 0 days.

(21) Appl. No.: 13/608,583

(22) Filed: Sep. 10, 2012

(65) Prior Publication Data
US 2013/0023857 A1 Jan. 24, 2013

Related U.S. Application Data

(63) Continuation of application No. 11/906,826, filed on Oct. 4, 2007, now Pat. No. 8,273,058.

(51) Int. Cl.
*A61B 17/50* (2006.01)
(52) U.S. Cl.
USPC .......................................................... 604/133
(58) Field of Classification Search
USPC ........... 604/181, 246, 891.1, 131–133, 890.1, 604/140, 141, 147
See application file for complete search history.

(56) References Cited

U.S. PATENT DOCUMENTS

| | | | |
|---|---|---|---|
| 4,431,425 A * | 2/1984 | Thompson et al. | 604/246 |
| 4,838,887 A * | 6/1989 | Idriss | 604/891.1 |
| 5,049,141 A | 9/1991 | Olive | |
| 5,088,515 A | 2/1992 | Kamen | |
| 5,281,210 A | 1/1994 | Burke et al. | |
| 5,669,764 A | 9/1997 | Behringer et al. | |
| 2005/0070875 A1 | 3/2005 | Kulessa | |
| 2006/0271022 A1 | 11/2006 | Steinbach et al. | |

OTHER PUBLICATIONS

International Search Report dated Mar. 5, 2009, issued in US Application No. PCT/US2009/00491, mailed on Mar. 17, 2009.

* cited by examiner

*Primary Examiner* — Bhisma Mehta
*Assistant Examiner* — Bradley Osinski
(74) *Attorney, Agent, or Firm* — The Marbury Law Group, PLLC

(57) ABSTRACT

An improved implantable valve accumulator pump for the delivery of medication is disclosed. The implantable pump comprises a pressurized drug reservoir. The medication metering assembly comprises a fixed volume accumulator positioned between a pair of valves. The valves alternately open and close to admit medication from the reservoir into the accumulator and to dispense a precise volume pulse to an outlet catheter. In order to improve the pump's accuracy and to increase pumping volume while optimizing the pump's overall size and energy usage a two way diaphragm accumulator is used. The unit can be externally programmed or can be used in a fixed rate configuration that is never programmed but set at the factory or in the current programmable configuration.

18 Claims, 4 Drawing Sheets

TWO WAY ACCUMULATOR PROGRAMMABLE VALVE PUMP

RELATED APPLICATIONS

The present application is a continuation of U.S. patent application Ser. No. 11/906,826 (issuing as U.S. Pat. No. 8,273,058), filed Oct. 4, 2007, the entire contents of both of which are hereby incorporated by reference.

BACKGROUND

This invention is a direct improvement over the technology of U.S. Pat. Nos. 4,838,887 and 5,049,141, the disclosures of which are hereby incorporated by reference. U.S. Pat. Nos. '887 and '141 describe a programmable valve pump overcoming many of the problems of the prior art employing an accumulator with a diaphragm that deflects in one direction when filling with medication and returning to a non-deflected state when emptying the accumulator. This is demonstrated in FIG. 2A of each of these patents. In each case, initial "pumping" is provided by the reservoir which is used to fill the accumulator to its fixed volume. A pressure which is intermediate between the reservoir and the outlet is maintained behind the accumulator so that it fills and empties completely and rapidly. The accumulator is alternately filled and emptied by the alternate switching of the valves. The rate of switching governs the rate of pumping and thus the delivery rate.

Switching is accomplished by onboard electronics powered by an internal battery. Once the battery is depleted, or if the battery is rechargeable and it cannot be recharged to an operational level, such devices need to be explanted and replaced with a new device. Extending the life of the pump through energy efficiency is critical in the design of such devices. Energy efficiency can be achieved by increasing the fixed volume pumped. Increasing the volume pumped can be achieved by increasing the size of the accumulator in diameter and/or height. However, increased accumulator size can create performance degradation of the existing designs. For example, a higher accumulator requires the accumulator diaphragm to deflect further. This increase in deflection creates a corresponding increase in diaphragm spring force. This in turn would have a cascading effect on design including the need to increase the intermediate accumulator and reservoir pressures and to increase the robustness of the pumps design and materials due to the increased pressure. These changes would adversely affect the size and weight of the implant, which by design, should be as small and light as practicable and would also adversely affect manufacturing costs and efficiencies. They would also adversely affect the filling pressure of the pump, would require the diaphragm to be prohibitively thin, making it hard to manufacture and to meet the life expectancy requirement for such a device. In addition, a one-way accumulator limits the maximum pulse size of drug delivery.

An object of this invention is to affect energy efficiency, increase fixed volume pumping and pump performance through a new accumulator design while minimizing the aforesaid adverse effects. The new design employs a "Two Way Diaphragm" that deflects in two directions.

SUMMARY

The problems of the prior art have been overcome by the present invention, which provides an infusion apparatus comprising a metering assembly that includes a valve accumulator pump, the infusion apparatus being implantable into a living body. More specifically, the invention relates to an infusion apparatus and to a metering assembly including a valve accumulator device for such apparatus that delivers precise amounts of medication or other fluid at programmed rates. The valve accumulator pump comprises two valves in fluid communication with a fixed volume accumulator. The valves alternately open and close to admit medication from an infusate reservoir into the accumulator and to dispense a precise volume pulse to an outlet catheter or the like. In order to improve the accuracy of the pump and to increase pumping volume while optimizing the overall size and energy usage of the pump, a two-way diaphragm accumulator is used.

In certain embodiments, the accumulator includes a chamber housing a diaphragm. The diaphragm provides a barrier between a gas portion of the chamber, and a liquid (infusate) portion of the chamber. When the chamber is devoid of liquid (e.g., the infusate has been discharged), the diaphragm is in a resting position. Upon opening the inlet valve, infusate under pressure enters the fluid portion of the chamber and urges the diaphragm against the bias of the gas in a first (e.g., upward) direction to fill the chamber with infusate. The inlet valve is then closed, and upon opening the outlet valve, the gas urges the diaphragm in a second (e. g., downward) direction, forcing the infusate out of the chamber.

BRIEF DESCRIPTION OF THE DRAWINGS

The accompanying drawings, which are incorporated herein and constitute part of this specification, illustrate exemplary aspects of the invention, and, together with the general description given above and the detailed description given below, serve to explain features of the invention.

DETAILED DESCRIPTION

Figure 1:
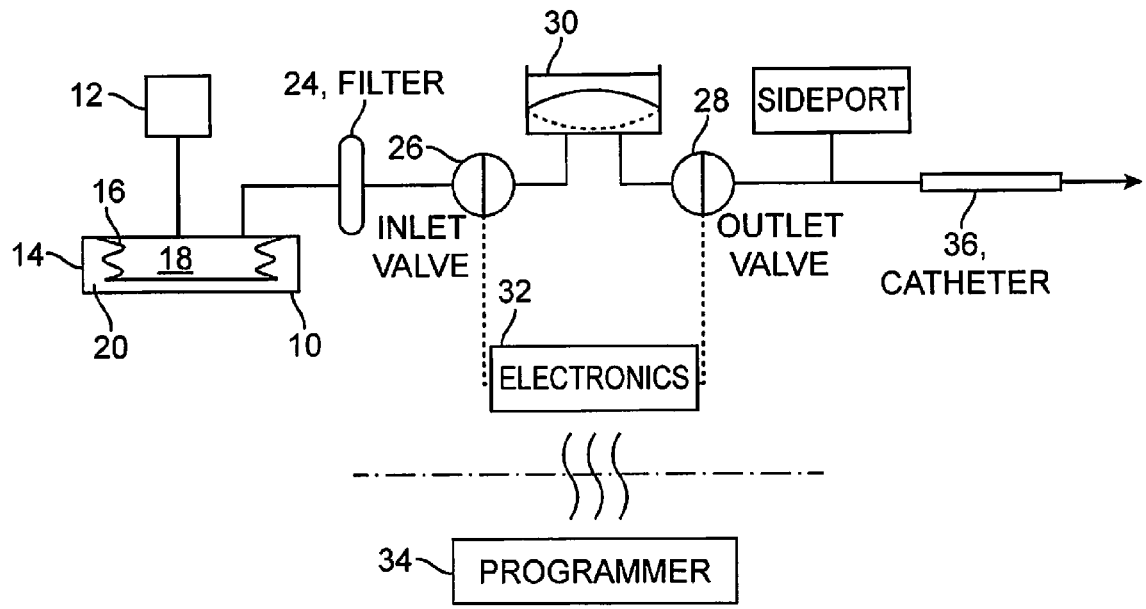
FIG. 1 is a schematic diagram of an infusion device in accordance with certain embodiments of the present invention.

As seen in FIG. 1, the infusion apparatus of the present invention includes a metering assembly having a programmable valve accumulator pump 30, an infusate reservoir 10 that can be conventional and well-known in the art, and an external programmer 34. Those skilled in the art will appreciate that an external programmer is not necessary; for example, the device could be used in a fixed rate configuration that is never programmed but is preset. The reservoir 10 is a sealed housing 14 that contains bellows 16 that includes an internal volume that contains the medicament or other fluid to be infused. The reservoir is preferably rechargeable such as via septum 12. External of the bellow is a chamber 20 that contains a fluid, such as a two-phase fluid having a significant vapor pressure at normal body pressure so that it compresses the bellows and causes the fluid in the bellows to exit the outlet of the housing 14. The outlet communicates with the metering assembly, such as via a bacterial filter 24, the metering assembly generally comprising an accumulator 30 and an inlet valve 26 and an outlet valve 28 in fluid isolation from the inlet valve. Preferably the metering assembly is electronically controlled in accordance with convention.

Figure 4:
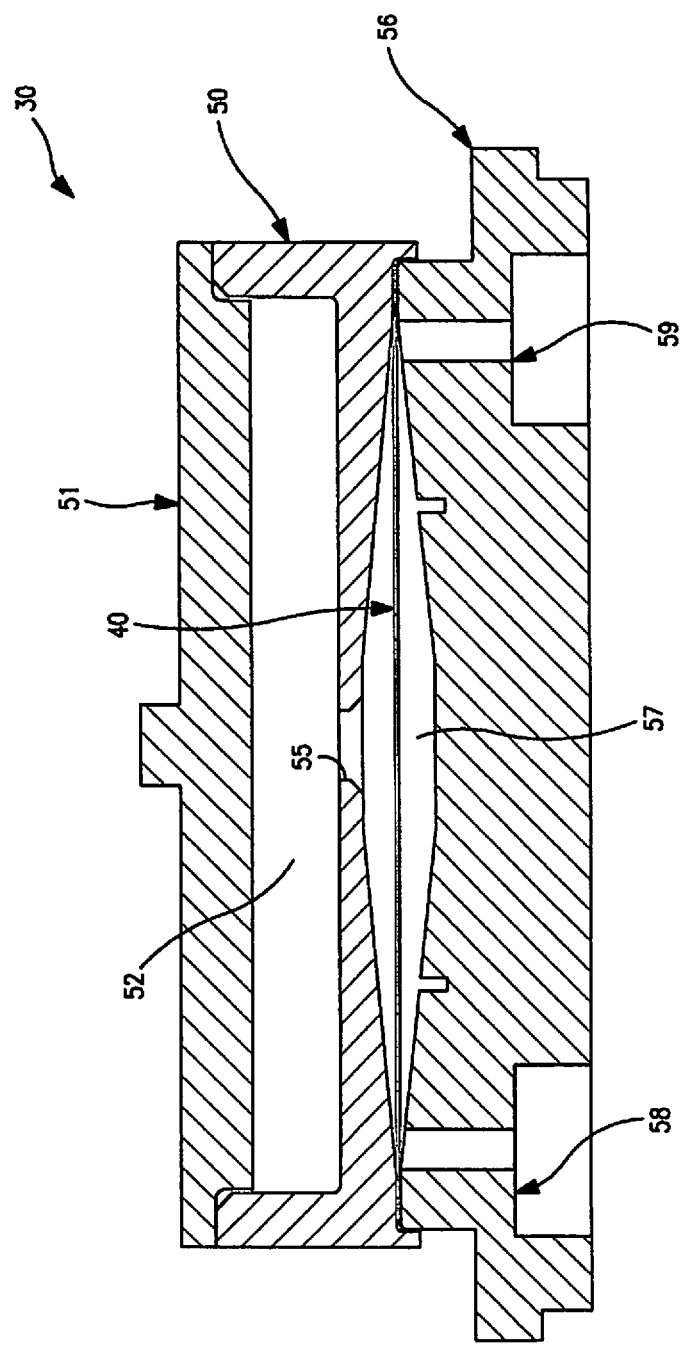
FIG. 4 is a cross-sectional view of an accumulator in accordance with certain embodiments of the present invention.
Figure 5:
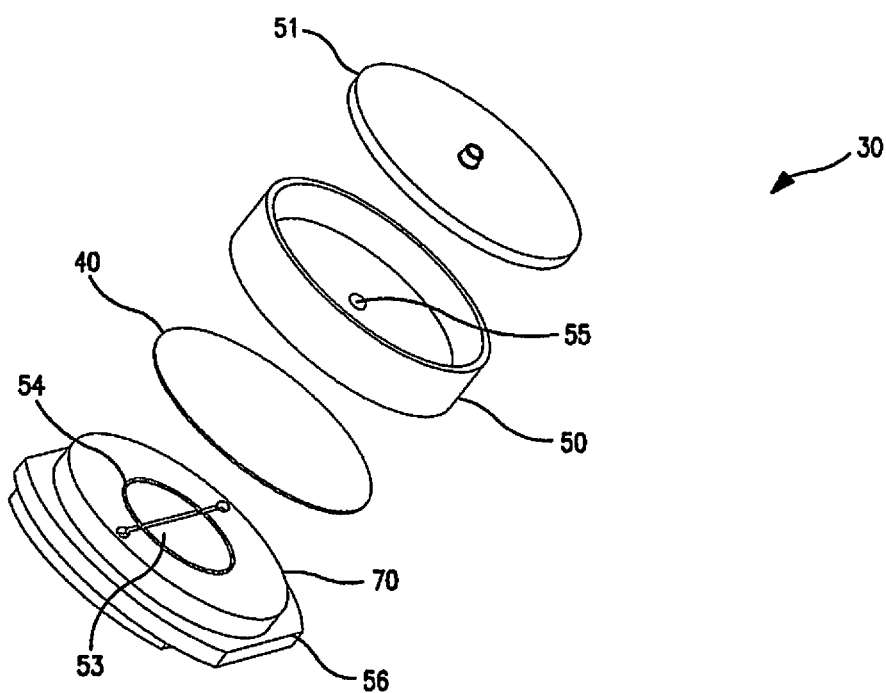
FIG. 5 is an exploded perspective view of an accumulator in accordance with certain embodiments of the present invention.

Turning now to FIGS. 4 and 5, accumulator 30 is shown. The accumulator 30 includes a housing 50, that together with cap 51 defines a sealed gas chamber 52. The cap 51 is attached to the housing 50 by any suitable means, such as laser welding. A suitable gas is sealed, under positive pressure, in the gas chamber 52. The gas chamber 52 is in fluid communication with diaphragm chamber 57 via a port 55 in the housing 50. The bottom surface of the housing 50 is configured and positioned to serve as a mechanical stop for the diaphragm 50 when the diaphragm 50 is in the up (fill) position.

Affixed to the housing 50 is a faceplate 56. Preferably the edges of the diaphragm 40 are sandwiched between the housing 50 and faceplate 57 as shown, and the assembly is sealed, such as by laser welding. The volume between the housing 50 and faceplate 57, containing the diaphragm 40, defines the diaphragm chamber 57. The diaphragm 40 thus provides a barrier, separating the gas side (e.g., above the diaphragm) from the fluid side (e.g., below the diaphragm) in the accumulator 30. Faceplate 56 also includes a fluid inlet port 58 that provides fluid communication between inlet valve 26 and the diaphragm chamber 57, and fluid outlet port 59 that provides fluid communication between outlet valve 28 and the diaphragm chamber 57.

Figure 2:
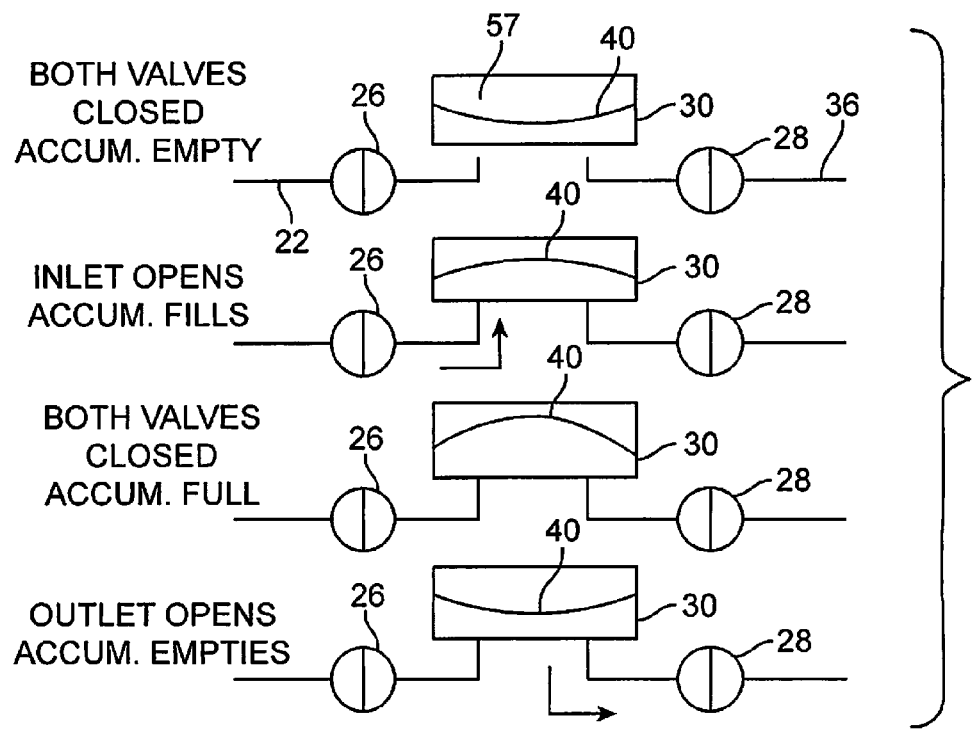
FIG. 2 is a schematic diagram of a having a two way diaphragm in accordance with certain embodiments of the present invention.

Turning now to FIG. 2, the operation of the accumulator assembly is shown schematically. A normally closed inlet valve 26 is in fluid communication with the inlet port 58 of the accumulator 30 (and the outlet of the reservoir 10 via line 22). A normally closed outlet valve 28 is in fluid communication with the outlet port 59 of the accumulator 30. Miniature solenoid valves are suitable. Preferably the valves 26, 28 are controlled electronically, such as through a module programmed by an external programmer 34 (FIG. 1). The outlet of the accumulator 30 communicates with a catheter or the like via line 36 that delivers the infusate to the delivery site in the patient in a conventional manner.

The diaphragm 40, as illustrated in FIGS. 2 and 4, is a circular disk of a thin metal sheet. Preferably titanium may be used, although other materials also may be suitable as determined by those skilled in the art. The disk is selected to have a diameter and thickness of low spring rate over the desired range of deflection. Thus, the diaphragm acts as a compliant, flexible wall which separates fluid from the environment behind it. The upward and downward motions of the diaphragm 40 are limited by the bottom surface of the housing 50, and the top surface of the faceplate 56, each of which serves as a mechanical stop for the diaphragm, depending on whether the diaphragm chamber 57 is filled with infusate or is empty of infusate. Thus, these surfaces are provided with a shallow concave profile manufactured into its diaphragm contact surface. This surface acts as a contour stop for the diaphragm. Dimensions of the contour are chosen to match the general profile of the diaphragm when it is deflected or biased by a predetermined fixed volume. This predetermined fixed volume is the volume desired to be metered from the accumulator (e.g., 2 µl)

Deflection of the diaphragm 40 occurs in both the upward and downward direction. The fixed volume pumped is essentially twice that pumped by a diaphragm of the same size that is only deflected in one direction in the same accumulator package configuration. Thus, the Two Way Diaphragm permits the optimization of accumulator size and energy utilization to increase fixed volume pumping and to conserve battery energy. The first step in the FIG. 2 pumping cycle shows the accumulator 30 in a state where both the inlet valve 26 and the outlet valve 28 are closed, and the diaphragm chamber 57 of the accumulator is empty (i.e., devoid of infusate fluid). In this condition, preferably the diaphragm 40 is firmly held against the spacer 70 by the gas and is substantially flat; it is not being urged or deflected in either an upward or downward direction (it is noted that the accumulator pressure is generally less than the reservoir pressure and diaphragm spring force and greater than the catheter outlet pressure). The second step in the cycle shows the accumulator 30 after the inlet valve 26 has been opened (maintaining the outlet valve 28 closed). The infusate fluid overcomes the bias of the pressurized gas against the diaphragm 40, and deflects the diaphragm 40 upward, thereby filling the diaphragm chamber 57 with fluid from the reservoir 10. The third step in the cycle is the closing of the inlet valve 26 once the diaphragm chamber 57 has been filled to its fixed or desired volume. The fourth step in the cycle is the opening of the outlet valve 28 (while maintaining the inlet valve 26 in the closed position) to empty the diaphragm chamber 57 through the catheter 36, wherein the diaphragm 40 deflects downward as a result of the bias from the gas pressure in the gas chamber 52 and in the gas side of the diaphragm chamber 57. Accordingly, the diaphragm 40 deflects in a first direction during the filling operation of the accumulator 30, as infusate fluid under pressure forces the diaphragm upwards against the mechanical stop of the bottom surface of the housing 50, overcoming the pressure exerted by the gas in the accumulator. The diaphragm also deflects in a second direction during the emptying of the accumulator 30, past its flat, resting point position, as the pressurized gas in the accumulator forces the diaphragm downward against the mechanical stop of the top surface of the faceplate 56. The two-way deflection allows twice the volume to be delivered during a single pumping cycle compared to conventional designs, using the substantially same amount of energy. Preferably the first and second directions of deflection of the diaphragm are opposite directions. The accumulator 30 thus stores and discharges predetermined volume spikes of infusate at a frequency defined by the cycling rate of the inlet and outlet valves.

Since the metering assembly controls the flow of fluid from the reservoir and does not rely on constant pressure to initiate flow, although a two-phase liquid can be used in the reservoir, a one-phase gas is suitable as well. Suitable gasses include inert gases such as argon, helium and nitrogen, mixtures thereof, and air.

FIGS. 5A and 5B of the '887 patent illustrate the details of the spacer plate utilized between the medication accumulation chamber and the accumulator valves. As disclosed in the '887 patent, the continuous contoured surface desirable to use on the gas-filled side of the diaphragm is undesirable on the fluid side. Intimate contact of two relatively flat surfaces with a liquid interface will create flow restrictions when the accumulator is emptied as the plates move toward each other and during filling when the plates move away from each other. This adverse effect was designed to be overcome by the addition of a checkerboard groove pattern as illustrated in FIG. 5B of the '887 patent. Additionally, a circumferential groove was incorporated in the design to establish fluid communication between the inlet and the outlet valves. Objects of the design were to: permit complete free flow of fluid underneath the flattened diaphragm; assist in washing of areas which might otherwise remain stagnant, and; maintain the accumulator dead volume at a minimum level.

U.S. Pat. No. 5,049,141 introduced an improved spacer plate design as illustrated in FIGS. 5A and 5B of that patent, the purpose of which was to reduce the diaphragm contact area with the plate. It was found that the prior art's use of a checkerboard groove provided too much surface contact area and therefore large molecule drugs could be crushed at the plate and diaphragm contact points resulting in the creation of drug residue. The prior art checkerboard design also created areas where the drug could stagnate and particles and air bubbles could be trapped. The '141 patent introduced an improved spacer plate design utilizing concentric circumferential grooves to establish fluid communication between the inlet and outlet valves and for fluid communication with the trough and a design that would reduce the diaphragm and plate contact area.

Figure 3:
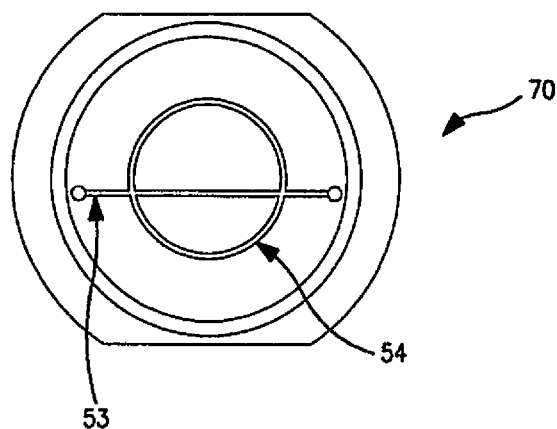
FIG. 3 is a top view of a spacer plate in accordance with certain embodiments of the present invention.

The spacer 70 in accordance with certain embodiments of the present invention improves upon the prior art with a design that maximizes the wash out of fluid and minimizes dead volume. Channels in the spacer are designed to create a flow path that allows the fluid to exit the accumulator quickly (e. g., the channel flow restriction is kept large enough to allow the accumulator to empty in a short period of time). It was found that the multiple annular grooves of the prior art provided multiple sites for stagnant fluid and air encapsulation resulting in dead volume and a degradation of pumping accuracy. As seen in FIGS. 3 and 5, the spacer 70 of the present invention includes an annular groove 54 intersected by (and thereby in fluid communication with) a trough 53 connecting the inlet and outlet valves wherein the volume of the space created by the annular and trough grooves permits the dead volume in the grooves and outlets to be equal to or less than about 5% of the total volume discharged by the accumulator. Preferably only a single annular groove 54 is provided, and it is interior to the inlet and outlet apertures respectively communicating with the inlet and outlet valves, such that the diameter of the annular groove 54 is smaller than the length of the trough 53. The groove 54 thus provides an annular flow path, and the trough 53 provides a lateral flow path between the inlet and outlet of the accumulator. Fluid in the groove 54 thus communicates with the inlet and outlet of the accumulator only through communication with the trough 53. The remaining peripheral surface of the space plate 50 is preferably flat. The new design flow path configuration and placement also allows for the fluid to flow out of the accumulator without adversely affecting the empty time.

What is claimed is:

1. An implantable infusion apparatus, comprising:
   an infusate reservoir; and
   an accumulator in a fluid flow path between the infusate reservoir and an infusate delivery site, the accumulator storing and discharging predetermined volume spikes of infusate, the accumulator comprising:
   a first surface defining a first mechanical stop;
   a spacer having a concave surface defining a second mechanical stop, the concave surface comprising an annular groove and a trough in fluid communication with the annular groove, wherein the annular groove is the only annular groove in the concave surface and wherein a diameter of the annular groove is smaller than a length of the trough, and the total volume of the space within the annular groove and the trough provides a dead volume in the accumulator that is equal to or less than 5% of the total volume of infusate discharged by the accumulator; and
   a metal diaphragm between the first surface and the spacer, the diaphragm having a resting state position, deflects in a first direction to contact against the first mechanical stop when infusate flows into the accumulator, and deflects in a second direction to contact against the second mechanical stop when infusate is discharged from the accumulator, wherein said first direction and said second direction are different.

2. The implantable infusion apparatus of claim 1, further comprising:
   a valve accumulator pump programmed to selectively actuate an inlet valve to cause infusate to flow into the accumulator and deflect the diaphragm in the first direction and against the first mechanical stop, and to selectively actuate an outlet valve to cause infusate to flow out of the accumulator and deflect the diaphragm in the second direction and against the second mechanical stop.

3. The implantable infusion apparatus of claim 1, further comprising:
   an opening in the spacer plate for discharging infusate from the accumulator.

4. The implantable infusion apparatus of claim 3, wherein the opening is located in the trough.

5. The implantable infusion apparatus of claim 3, wherein the opening is in communication with a valve.

6. The infusion apparatus of claim 1, wherein the accumulator stores and discharges the predetermined volume spikes at a frequency that is determined by a cycling rate of at least one valve.

7. The infusion apparatus of claim 1, further comprising a first opening in the spacer plate for introducing infusate into the accumulator and a second opening in the spacer plate for discharging infusate from the accumulator, wherein the first opening and the second opening are located in the trough.

8. The implantable infusion apparatus of claim 1, wherein the accumulator comprises an accumulator cap such that a sealed chamber is defined between the accumulator cap and the diaphragm, the first mechanical stop being located within the sealed chamber, and wherein gas is sealed under positive pressure within the sealed chamber.

9. The implantable infusion apparatus of claim 8, wherein the diaphragm moving in two directions and the sealed chamber via the accumulator cap increases fixed volume pumping and conserves battery energy of the infusion apparatus.

10. The implantable infusion apparatus of claim 1, wherein the trough is the only trough in the second concave surface.

11. An implantable infusion apparatus, comprising:
    an infusate reservoir; and
    an accumulator in a fluid flow path between the infusate reservoir and an infusate delivery site, the accumulator storing and discharging predetermined volume spikes of infusate, the accumulator comprising:
    a first surface defining a first mechanical stop;
    a spacer having a concave surface defining a second mechanical stop, the concave surface comprising an annular groove and a trough in fluid communication with the annular groove, wherein the annular groove is the only annular groove in the concave surface, and the total volume of the space within the annular groove and the trough provides a dead volume in the accumulator that is equal to or less than 5% of the total volume of infusate discharged by the accumulator;
    a first opening in the spacer plate for introducing infusate into the accumulator and a second opening in the spacer plate for discharging infusate from the accumulator, wherein the first opening and the second opening are located in the trough, and wherein a diameter of the annular groove is smaller than a distance from the first opening to the second opening; and
    a metal diaphragm between the first surface and the spacer, the diaphragm having a resting state position, deflects in a first direction to contact against the first mechanical stop when infusate flows into the accumulator, and deflects in a second direction to contact against the second mechanical stop when infusate is discharged from the accumulator, wherein said first direction and said second direction are different.

12. A method of delivering infusate to a delivery site within a living body using an implantable infusion apparatus, comprising:

introducing a volume of infusate into a diaphragm chamber to cause a metal diaphragm in the chamber to deflect from a resting state position in a first direction to contact against a first concave surface defining a first mechanical stop; and discharging the volume of infusate from the diaphragm chamber such that the metal diaphragm deflects from the resting state position in a second direction to contact against a second concave surface comprising an annular groove and a trough in fluid communication with the annular groove, the second direction being different from the first direction, wherein the annular groove is the only annular groove in the second concave surface and a diameter of the annular groove is smaller than a length of the trough, and the total volume of the space within the annular groove and the trough provides a dead volume in the chamber that is equal to or less than 5% of the total volume of infusate discharged from the chamber.

13. The method of claim 12, wherein introducing infusate into the diaphragm chamber comprises controlling a first valve coupled to an opening in the concave surface.

14. The method of claim 13, wherein the opening is located in the trough.

15. The method of claim 12, wherein discharging infusate from the diaphragm comprises controlling a second valve coupled to an opening in the concave surface.

16. The method of claim 15, wherein the opening is located in the trough.

17. An accumulator for an implantable infusion apparatus for delivering infusate, comprising:

a diaphragm chamber having a first concave surface defining a first mechanical stop and a spacer having a second concave surface defining a second mechanical stop, the concave surface comprising an annular groove and a trough in fluid communication with the annular groove, wherein the annular groove is the only annular groove in the concave surface and a diameter of the annular groove is smaller than a length of the trough; and a metal diaphragm disposed in the diaphragm chamber, the diaphragm having a resting state position, deflects in a first direction relative to the resting state position to contact against the first mechanical stop when infusate flows into the accumulator, and deflects in a second direction relative to the resting state position to contact against the second mechanical stop when infusate is discharged from the accumulator, wherein said first direction and said second direction are different, and wherein the total volume of the space within the annular groove and the trough provides a dead volume in the accumulator that is equal to or less than 5% of the total volume of infusate discharged by the accumulator.

18. An implantable infusion apparatus comprising:

a housing containing an infusate reservoir, a metering assembly receiving infusate from the infusate reservoir, the metering assembly comprising at least one valve and an accumulator positioned in fluid communication with the at least one valve, the accumulator comprising a chamber having a first concave surface defining a first mechanical stop and a second concave surface defining a second mechanical stop and containing a metal diaphragm separating the chamber into a gas portion and a liquid portion, the metal diaphragm having a resting position, deflects in a first direction relative to the resting position, and deflects in a second direction relative to the resting position, wherein the first direction and the second direction are different, and an outlet in fluid communication with the metering assembly to dispense infusate to a site in a living body; and a valve accumulator pump programmed to selectively actuate the at least one valve to cause infusate to flow into the liquid portion and deflect the diaphragm in the first direction and against the first mechanical stop, and to cause infusate to flow out of the liquid portion and deflect the diaphragm in the second direction and against the second mechanical stop, wherein the accumulator further comprises a spacer, the spacer having the second concave surface defining the second mechanical stop, the second concave surface comprising an annular groove and a trough in fluid communication with the annular groove and with the outlet of the accumulator, wherein the annular groove is the only annular groove in said second concave surface and a diameter of the annular groove is smaller than a length of the trough and the total volume of the space within the annular groove and the trough provides a dead volume in the accumulator that is equal to or less than 5% of the total volume of infusate discharged by the accumulator.

* * * * *